United States Patent [19]

Gerwick

[11] Patent Number: 4,935,529
[45] Date of Patent: Jun. 19, 1990

[54] CYTOXIC SUBSTANCES FROM THE MARINE CYANOPHYTE HORMOTHAMNION ENTEROMORPHOIDES GRUNOW

[75] Inventor: William H. Gerwick, Philomath, Oreg.

[73] Assignee: State of Oregon acting by and through the Oregon State Board of Higher Education on behalf of Oregon State University, Eugene, Oreg.

[21] Appl. No.: 320,007

[22] Filed: Mar. 6, 1989

Related U.S. Application Data

[63] Continuation of Ser. No. 825,138, Jan. 31, 1986, abandoned.

[51] Int. Cl.$^5$ ............................................. C07D 311/22
[52] U.S. Cl. .................................................... 549/401
[58] Field of Search ......................................... 549/401

[56] References Cited

U.S. PATENT DOCUMENTS 4,281,008  7/1981  Chamberlain et al. ............. 549/401

OTHER PUBLICATIONS

Gerwick et al., C.A. 105, 75478g (1986).
Alonso et al., Tetrahedron Letters, 29, 735–738 (1988).
Suffness et al., J. Nat. Prod. 45, 1–14 (1982).

*Primary Examiner*—Nicky Chan
*Attorney, Agent, or Firm*—Klarquist, Sparkman, Campbell, Leigh & Whinston

[57] ABSTRACT

Several new, biologically active substances have been isolated from *Hormothamnion enteromorphoides*, a somewhat rare cyanophyte from Puerto Rico.

Hormothamnion, a lipophilic metabolite from this alga, has the styrylchromone structure:

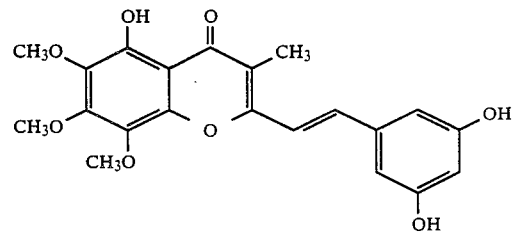

Hormothamnion and, to a lesser extent, one of its homologs, are potent cytotoxins to some types of cancer cells and appear to exert this cytotoxic action by a selective inhibition of RNA synthesis.

A peptide compound of about 11 to 12 amino acids has antimicrobial activity, particularly against *Candida albicans*. The peptide, which includes phenylalanine, serine and other aliphatic amino acids, has blocked carboxyl and amino termini.

1 Claim, 1 Drawing Sheet

CYTOXIC SUBSTANCES FROM THE MARINE CYANOPHYTE HORMOTHAMNION ENTEROMORPHOIDES GRUNOW

This invention was made with government support under S.E.A. Grant Project No. R/PD-47 awarded by the National Oceanographic and Atmospheric Administration. The government has certain rights in this invention.

This is a continuation of application Serial No. 06/825,138, filed Jan. 31, 1986, now abandoned.

SUMMARY OF THE INVENTION

The present invention relates to biologically active substances obtainable from Cyanophyta, and more particularly to the chromone metabolites and peptides thereof.

The search for new structure types from marine organisms with potential drug activity has intensified in recent yars, and has recently centered on several ecific taxonomic groups, one of which is the Cyanophyta.

As described in the following publications, blue green algae have recently received considerable attention by academic researchers, the National Cancer Institute, and industry as a new source of novel bioactive natural products: Carter et al, *J. Org. Chem.* 49: 236-244 (1984); Moore et al., *J. Am. Chem. Soc.*, 106: 6456-6457 (1984); Barchi et al., *J. Am. Chem. Soc.*, 106: 8193-8197 (1984); Cragg et al., *Am. Soc. Pharmacog. Proceedings*, abs. no. 185 (1985); 1984 Prospectus, Sea Pharm, Inc., Ft. Pierce, Fla. Carter et al. have reported an abundance of unique secondary metabolites from the principal mat-forming marine cyanophyte, *Microcoleus lyngbyaceus* (syn *Lyngbya majuscula*).

Previously, styrylchromone structures have not been found in natural products although the carbon skeleton is known from synthetic studies as reported by G. P. Ellis in "Alkylchromones" in *Heterocyclic Compounds: Chromenes, Chromanones and Chromones*, (Ellis, G. P., ed., John Wiley and Sons, New York, 1977, pp. 581-631).

It has now been found that *Hormothamnion enteromorphoides*, a somewhat rare cyanophyte from Puerto Rico, yields certain biologically active compounds.

A new lipophilic metabolite, named hormothamnion, is found to have a styrylchromone structure, which is without precedent among known natural products. Hormothamnion is a potent cytotoxin to some types of cancer cells ($IC_{50}=0.2$ ng/ml to the HL 60 cell line in tissue culture). It, and to a lesser extent, one homologous compound appear to exert this cytotoxic action by a selective inhibition of RNA synthesis. Hormothamnion represents the first of a new class of cytotoxins which are readily synthesizable.

DETAILED DESCRIPTION

Figure 1:
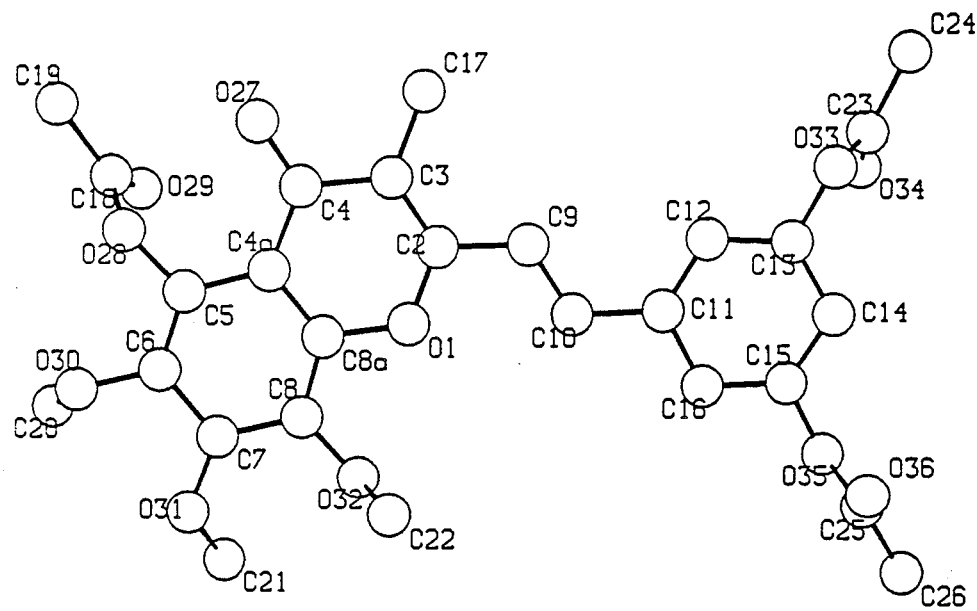
FIG. 1 is a perspective drawing of an x-ray model of hormothamnion triacetate.

The marine cyanophycean alga *Hormothamnion enteromorphoides* Grunow (Nostocaceae) is one of only a few blue greens which form dense mats in shallow tropical marine environments. *H. enteromorphoides* as described herein was collected from the exposed north coast of Puerto Rico.

The present invention concerns styrylchromones of the formula:

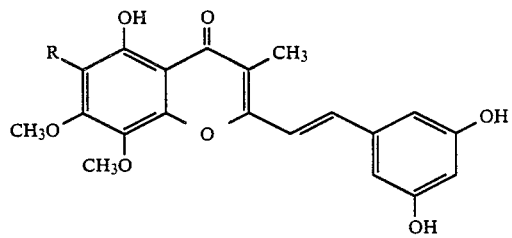

wherein R is —H or —OCH$_3$.

At least two styrylchromone compounds from *H. enteromorphoides* were found to have antineoplastic drug activity.

EXAMPLE 1

A CHCl$_3$/MeOH extract of fresh *H. enteromorphoides* demonstrated slight gram positive antimicrobial activity and showed the presence of a distinctive orange-charring (H$_2$SO$_4$) yellow pigment by thin layer chromatography. The readily isolable pigment band contained a subtle mixture of several compounds, the major of which was isolated by careful reverse phased HPLC and its novel styrylchromone structure (FIG. 1) solved by x-ray crystallographic means. Trivially named hormothamnion, this metabolite is a potent cytotoxin to several human cancerous cell lines and appears to operate via inhibition of RNA synthesis (Table I).

TABLE I

Inhibition of Cell Growth and Macromolecule Biosynthesis in Several Cancerous Human Cell Lines by Hormothamnione (1)

| Cell-line | $ID_{50}$ (ng/ml)$^a$ Cell Growth | $ID_{50}$ (ng/ml)$^{bc}$ DNA | $ID_{50}$ (ng/ml)$^{bd}$ RNA | $ID_{50}$ (ng/ml)$^{be}$ Protein |
|---|---|---|---|---|
| P-388 | 4.6 | — | — | — |
| HL-60 | 0.1 | 300 | 1.0 | >500 |
| KB | — | 530 | 140 | >500 |

$^a$$ID_{50}$ is the drug concentration required to inhibit cell growth to 50% of control levels.
$^b$The percentages of macromolecule biosynthesis inhibition were calculated from the specific activities of incorporated precursors (c-e) into 10$^6$ cells in drug treated as versus control cells. $ID_{50}$ values were obtained by plotting the logarithmic drug concentrations against the percentage inhibition of macromolecule biosynthesis.
$^c$Exponentially growing cells pulse labeled with 1 μCi of $^3$H-thymidine (16.6 Ci/mmole) per ml of cell suspension.
$^d$Exponentially growing cells pulse labeled with 2 μCi [5-$^3$H]-uridine (28 Ci/mmole) per ml of cell suspension.
$^e$Exponentially growing cells pulse labeled with 1 μCi of $^3$H-L-leucine (130 Ci/mmole) per ml of cell suspension.

Senescent yellow-colored *H. enteromorphoides* was found in abundance on an exposed shallow reef (1–3 m) at Playa de Vega Baja, Puerto Rico several times during the months of July and August in 1984 and 1985. The frozen or alcohol preserved seaweed was extracted in standard fashion (CHCl$_3$/MeOH 2:1) and the yellow pigment band containing hormothamnion was isolated by vacuum chromatography over TLC grade silica gel. Preparative thick layer chromatography of this yellow band simplified the mixture to two components of 75:25 ratio. Small quantities of hormothamnion were obtained from this mixture employing painstaking reverse phased HPLC conditions using two Waters 3.9 mm×25 cm μ-Bondapak C-18 columns in series, 40 percent H$_2$O/-MeOH as mobil phase, 1.5 ml min., 35 min. retention time, 0.5 mg per injection. Hormothamnion was easily reformed (as determined by TLC, MS, NMR) via mild base treatment (K₂KO₃ in MeOH) of the derivative. The relative ease in purification of the derivative and its more favorable solubility properties were factors in deciding to work largely with the derivative rather than the natural product. Formulas of the natural product, hormothamnion (1) and its derivative (2) are as follows:

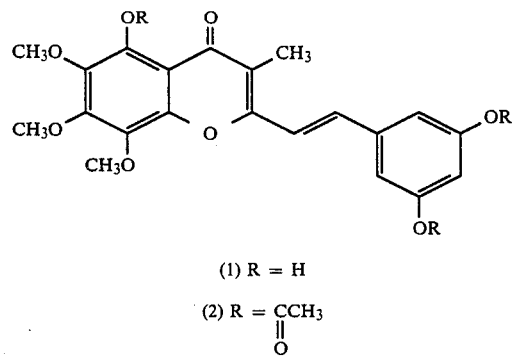

(1) R = H (2) R = CCH₃
         ‖
         O

Hormothamnion was a yellow solid (m.p. 270° C. dec) which analyzed for $C_{21}H_{20}O_8$ by high resolution election impact mass spectrometry (M+ M/Z400.1163, 46 percent) which upon derivatization increased in mass to $C_{27}H_{26}O_{11}$ (M+ =base peak at m/Z 526 by low resolution CIMS in the negative ion mode) and thus, the derivative was the triacetate derivative of hormothamnion. The natural product had typical chromone (Ellis, G. P., "Chromone uv absorptions and Its Benzo Derivatives" in *Heterocyclic Compounds: Chromenes, Chromanones and Chromones*, G. P. Ellis, ed., New York, 1977; pp. 557–580) at 295 and 353 nm (MeOH; ε=200; 8,900 respectively) and IR absorptions (KBr) broadly centered at 3400 cm⁻¹ (phenol) and at 1640 cm⁻¹ (pyrone carbonyl). The ¹H NMR (80 MHz, CDCl₃) of the derivative confirmed its triacetate nature [δ 2.34 (6H, s) and 2.50 (3H, s)].

Of the remaining seventeen hydrogens in the ¹H NMR spectrum of the derivative, twelve were present as methyl singlets, three at shifts consistent with aromatic methoxyls [δ 3.89 (3H, s), 4.06 (3H, s) and 4.11 (3H, s)] and one consistent with a deshielded olefinic methyl group [δ 2.17 (3H, s)]. The other 5 protons were separated into two deshielded spin systems, one consistent with a trans disubstituted olefin [δ 7.08 (1H, d, J=16) and δ 7.58 (1H, d, J=16)] and the other interpreted as forming the proton componen of a symmetrical 1,3,5 trisubstituted aromatic ring [δ 6.94 (1H, t, J=1.9) and 7.23 (2H, d, J=1.9)]. The nature of the ring system and placement of these proton, methyl, methoxy and acetoxy substituents was not readily determinable, and more definitive NMR experiments were precluded due to limited resources of compound. Hence, an x-ray experiment was performed to unambiguously assign the structure of the crystalline derivative (mp 198°–201° C.).

Preliminary x-ray photographs of the triacetate derivative displayed monoclinic symmetry and accurate lattice constants of a=18.472(5), b=5.769(3), c=24.096(6) Å, and β=93.40(2)° were determined from a least squares analysis of fifteen moderate, diffractometer measured 2θ-values. The systematic extinctions and crystal density indicated space group P2₁/a with one molecule of composition $C_{27}H_{26}O_{11}$ forming the asymmetric unit (Z=4). All diffraction maxima with 2θ< or =114° were measured on a computer controlled four-circle diffractometer with graphite monochromated Cu Kα radiation (1.54178 Å) and variable speed, 1° ω-scans. Of the 3459 reflections surveyed, only 1211 (35 percent) were judged observed ($F_o$> or =3σ($F_o$)) after correcton for Lorentz, polarization and background effects. The centrosymmetric structure was solved easily. Hydrogen atoms were located on a ΔF-synthesis after partial refinement of the nonhydrogen atoms. Block diagonal lease-squares refinements with anisotropic nonhydrogen atoms and isotropic hydrogens have converged to a standard crystallographic residual of 0.081 for the observed reflections.

A computer generated drawing of the final x-ray model of hormothamnion triacetate appears in FIG. 1. The chromone fragment (atoms 01 to C8a) is planar, and the substituents on the fully substituted aromatic ring are all rotated out of the plane. The relevant torsional angle vary from 50° for C8-C7-031-C21 to 87° for C7-C8-032-C22. The acetate substituents on the 1,3,5-substituted ring are also rotated by roughly 77°.

As indicated in Table I, hormothamnion was found to be a potent cytotoxic agent to P388 lymphocytic leukemia and HL-60 human promyelocytic leukemia cell lines. Macromolecule biosynthesis in the presence of hormothamnion was measured via radioactive precursor incorporation studies using HL-60 and KB cell lines. A major mode of cytotoxic action of hormothamnion appears to be by inhibition of RNA synthesis. Hormothamnion showed minimal gram positive antimicrobial activity when tested by the paper disc-agar plate method, using 100 μg and 25 μg of hormothamnion per 6 mm paper disc, tested against *Staphylococcus aureus* (−), *Bacillus subtilus* (10 mm zone at 100 μg, 8 mm zone at 25 μg), *Escherichia coli* (−) and *Candida albicans* (−).

EXAMPLE 2

A closely related styrylchromone compound was isolated and identified from the extract of Example 1 using the same procedures:

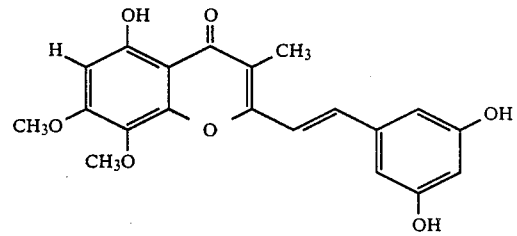

When tested, the compound of formula (3) also inhibited the growth of several human cell lines. But, the effect was less than observed with hormothamnion.

Styrylchromone substances can be administered to animal subjects in any convenient dosage form. Salts or esters of the compounds may be preferred for use in medications.

Multiple collections of *Hormothamnion enteromorphoides* from different seasons has shown that hormothamnion compounds are present only in yellow senescent growths of the alga found during the late summer. At other times of the year, the alga appears dark green and produces different natural products.

While I have shown and described the preferred embodiments of my invention, it will be apparent to those skilled in the and that changes and modifications may be made without departing from my invention in its broader aspects. I therefore intend the appended claims to cover all such claims and modifications as follow the true spirit and scope of my invention.
I claim:
1. A compound of the formula:
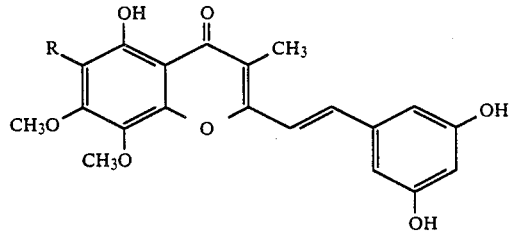
wherein R is —H or —OCH$_3$.